US011339426B2

(12) United States Patent
Kwon et al.

(10) Patent No.: US 11,339,426 B2
(45) Date of Patent: May 24, 2022

(54) METHOD CAPABLE OF DIFFERENTIATING FETAL SEX AND FETAL SEX CHROMOSOME ABNORMALITY ON VARIOUS PLATFORMS

(71) Applicant: EONE DIAGNOMICS GENOME CENTER CO., LTD., Incheon (KR)

(72) Inventors: Chang Hyuk Kwon, Gyeonggi-do (KR); Seon Young Yun, Gyeonggi-do (KR); Min Seob Lee, Incheon (KR)

(73) Assignee: EONE DIAGNOMICS GENOME CENTER CO., LTD.

( * ) Notice: Subject to any disclaimer, the term of this patent is extended or adjusted under 35 U.S.C. 154(b) by 954 days.

(21) Appl. No.: 15/750,002

(22) PCT Filed: Aug. 8, 2016

(86) PCT No.: PCT/KR2016/008679
§ 371 (c)(1),
(2) Date: Feb. 2, 2018

(87) PCT Pub. No.: WO2017/023148
PCT Pub. Date: Feb. 9, 2017

(65) Prior Publication Data
US 2019/0228131 A1    Jul. 25, 2019

(30) Foreign Application Priority Data
Aug. 6, 2015 (KR) .................. 10-2015-0111221

(51) Int. Cl.
*C12Q 1/6869* (2018.01)
*G16B 40/00* (2019.01)
(Continued)

(52) U.S. Cl.
CPC ......... *C12Q 1/6869* (2013.01); *C12Q 1/6876* (2013.01); *C12Q 1/6879* (2013.01);
(Continued)

(58) Field of Classification Search
CPC .............. C12Q 1/6869; C12Q 2537/16; C12Q 2537/165; C12Q 1/6827; C12Q 2535/122;
(Continued)

(56) References Cited

U.S. PATENT DOCUMENTS 10,497,461 B2 *  12/2019  Dzakula .................. G16B 20/00
10,699,800 B2 *   6/2020  Zhao ..................... C12Q 1/6869

FOREIGN PATENT DOCUMENTS

KR      20140108177 A      9/2014
KR      20150070111 A      6/2015
WO      WO-2014190286 A2 * 11/2014 ........... C12Q 1/6869

OTHER PUBLICATIONS

Gregg, A. R. et al. Noninvasive Prenatal Screening by Next Generation Sequencing. (published online May 14, 2014) Annual Reviews Genomics and Human Genetics vol. 15, pp. 327-347. (Year: 2014).*

(Continued)

*Primary Examiner* — Mary K Zeman
(74) *Attorney, Agent, or Firm* — Levenfeld Pearlstein, LLC (57) ABSTRACT

The present invention relates to a method capable of, in order to diagnose fetal sex chromosome aneuploidy, differentiating Kleinfeiter's syndrome (XXY), triple X syndrome (XXX), and Turner's syndrome (monosomy X, XO) as well as male (XY) and female (XX) by using copy number variation (CNV). The differentiation method according to the present invention has significantly high sensitivity and accuracy since the reference line is evenly adjusted by performing normalization regardless of the kinds of platform and data. The present invention is useful in diagnosing the sex chromosome abnormality at an early stage through easy diagnosis of sex chromosomes X and Y, which are hard to diagnose, since an analysis is possible even with a small amount of fetal chromosomes, which corresponds to an (Continued)

advantage of noninvasive prenatal diagnosis, and copies are redundant.

9 Claims, 9 Drawing Sheets

(51) Int. Cl.
*G16B 20/10* (2019.01)
*G16B 20/00* (2019.01)
*G16B 30/00* (2019.01)
*C12Q 1/6876* (2018.01)
*C12Q 1/6879* (2018.01)

(52) U.S. Cl.
CPC .............. *G16B 20/00* (2019.02); *G16B 20/10* (2019.02); *G16B 30/00* (2019.02); *G16B 40/00* (2019.02)

(58) Field of Classification Search
CPC .. C12Q 1/68; C12Q 2545/114; C12Q 1/6879; C12Q 2600/112; C12Q 2545/101; G16B 30/00; G16B 20/00; G16B 20/10; G16B 40/00; G16B 30/10; G16B 25/00; G16B 20/20; G16B 45/00; G16B 30/20; G16B 25/10; G16B 40/10; G16B 99/00; G16B 40/20; G16B 20/40; G16B 25/20; G16B 35/00; G16B 15/00; G16B 50/00; G16H 50/20; G16H 10/40; G16H 50/30; G16H 50/50; C40B 40/08; C40B 30/00; G06F 19/00; G06F 17/18; G06F 19/18; G06F 19/22; G01N 2800/385; G06N 20/00; G06N 3/08; G16C 20/60
See application file for complete search history.

(56) References Cited

OTHER PUBLICATIONS

Jiang, F. et al. Noninvasive Fetal Trisomy test: an advanced non-invasive prenatal diagnosis methodology for fetal autosomal and sex chromosomal aneuploidies. BMC Medical Genomics (2012) 5:57, 11 pages. (Year: 2012).*
Yin et al. Noninvasive detection of fetal subchromosomal abnormalities by semiconductor sequencing of maternal plasma DNA. PNAS vol. 112, No. 47, p. 14670-14675, published online Nov. 9, 2015. (Year: 2015).*
Liao, C. et al. Noninvasive prenatal diagnosis of common aneuploidies by semiconductor sequencing. PNAS vol. 111, No. 20 p. 7415-7420 (May 20, 2014). (Year: 2014).*
Chen, S. et al. Performance comparison between rapid sequencing platforms for Ultra-low coverage sequencing strategy. (Mar. 2014) PLOS One 9:3 e92192. (Year: 2014).*
Fox et al. Accuracy of Next Generation Sequencing Platforms. (2014) Next Generation Sequencing and Applications 1:1, e1000106. (Year: 2014).*
Wang et al. Comparison of Ion Torrent chips in non-invasive prenatal trisomy detection. (2014) Journal of Human Genetics 59: 393-396. (Year: 2014).*
Liao, Can et al., Noninvasive Prenatal Diagnosis of Common Aneuploidies by Semiconductor Sequencing, PNAS Journal, May 2014, pp. 7415-7420, vol. 111 No. 20, Proceedings of the National Academy of Sciences of the United States of America, Boston, MA.
Lo, Kitty K. et al., RAPIDR: an analysis package for non-invasive prenatal testing of aneuploidy, Bioinformatics Journal, Oct. 2014, pp. 2965-2967, vol. 30, Issue 20, International Society for Computational Biology, London, United Kingdom.
Fan, Christina H. et al., Sensitivity of Noninvasive Prenatal Detection of Fetal Aneuploidy from Maternal Plasma Using Shotgun Sequencing Is Limited Only by Counting Statistics, PLOS ONE Journal, May 3, 2010, p. 10439, vol. 5, No. 5, Brunel University, United Kingdom.

* cited by examiner

METHOD CAPABLE OF DIFFERENTIATING FETAL SEX AND FETAL SEX CHROMOSOME ABNORMALITY ON VARIOUS PLATFORMS

TECHNICAL FIELD

The present invention relates to a method for aneuploidy analysis of fetal sex and fetal sex chromosomes (for example, deletion and duplication of some regions in the sex chromosome X and Y regions of fetal genes), and discovery and verification thereof, using data obtained by performing next-generation sequencing (NGS) from various samples, wherein it is possible to obtain the same result even though heterogeneous data from various platforms are inputted.

BACKGROUND ART

From the 1970s until recently, diagnostic methods for diseases related to chromosome numerical abnormality have been continuously developed. In the past, amniotic examination or chorionic villus examination was recommended when the mother was 35 years or older. These techniques are known to be invasive methods in which a fetal loss rate is 1/100 to 1/300, accuracy is not high, and false positive rate and false negative rate are high. 95% or more of pregnant women classified as a high risk group are in need of more accurate and safe diagnostic testing methods in order to give birth to healthy babies.

In order to diagnose chromosome abnormalities and sex chromosome abnormalities, technologies with safety and high accuracy using next-generation sequencing analysis technology have been introduced from the late 2000s (Korean Patent Laid-open Patent Application No. 10-2010-7003969, No. 10-2012-7034453), wherein diagnosis of aneuploidy through sequencing of cell-free DNA (cfDNA) has advantages of high accuracy and low false negative rate, rather than traditional analysis methods.

Recently, a non-invasive prenatal test (NIPT) technology, which is an updated technology, is being carried out on the basis of the next-generation sequence analysis (NGS) (Bianchi D W et al., (2014) DNA Sequencing Versus Standard Prenatal Aneuploidy Screening. N. Engl. J. of Med. 370: 799-808., Sparks A B et al., (2012) Noninvasive Prenatal Detection and Selective Analysis of Cell-Free DNA Obtained from Maternal Blood: Evaluation for Trisomy 21 and Trisomy 18. Am. J. Obstet. Gynecol. 206: 319.e1-9., Ehrich, M. et al., (2011) Noninvasive Detection of Fetal Trisomy 21 by Sequencing of DNA in Maternal Blood: A Study in a Clinical Setting. Am. J. Obstet. Gynecol. 204: 205.e1-11), and a fast and efficient clinic analytical test is being conducted by using two platforms from Illumina and Ion Torrent companies. Sensitivity and specificity of the non-invasive prenatal test (NIPT) analysis using the Illumina platform at the beginning were about 98% (Lau, T. K. et al., (2014) Non-invasive Prenatal Testing for Fetal Chromosomal Abnormalities by Low-Coverage Whole Genome Sequencing of Maternal Plasma DNA: Review of 1982 Consecutive Cases in a Single Center. Ultrasound Obstet. Gynecol. 43: 254-264, Ashoor G et al., (2012) Chromosome-Selective Sequencing of Maternal Plasma Cell-Free DNA for First Trimester Detection of Trisomy 21 and Trisomy 18. Am. J. Obstet. Gynecol. 206: 322.e1-5). However, recent studies have shown that aneuploidy diagnostic sensitivity of fetal chromosomes 13, 18, and 21 using the HiSeq (Illumina) and the Ion Proton (Ion Torrent) is higher than 99.5% (Liao, C., et al., (2014) Noninvasive Prenatal Diagnosis of Common Aneuploidies by Semiconductor Sequencing. Proc. Natl. Acad. Sci. USA. 111: 7415-7420).

A number of chromosome related clinic diseases are associated with the number of copies of sex chromosomes as well as autosomal changes. The most common sex chromosome aneuploidy (SCA) is Turner syndrome [45, X], XXX syndrome (Triple-X [47, XXX]), Klinefelter syndrome [47, XXY], and Super male syndrome ([47, XYY] syndrome). These diseases are known to be have a relatively rare incidence, but have been reported that these diseases cause cumulative sex chromosome aneuploidy of about 0.3% (Morris, J. K., et al., Is The Prevalence of Klinefelter Syndrome Increasing; Eur. J. Hum. Genet. 2007; 16: 163-70). In a study of 115 patients in the pediatric department of Kyungpook National University Hospital for 20 years, the frequency of sex chromosome abnormality syndrome was 52% in Kleinfelder syndrome, 42% in Turner syndrome, 3% in XXX syndrome, and 3% in mixed gonadal dysplasia. Kleinfelder syndrome has 97% of typical XXY type and 3% of mosaicism, Turner syndrome has 67% of typical X type, 23% of mosaicism, and 10% of structural abnormality of the X chromosome. XXX syndrome has 67% of XXX type and 33% of mosaicism, and the mixed gonadal dysplasia is all 45,X/46,XY (Seo, Hyun ji et al., a cytogenetic study in patients with sex chromosome abnormalities, Korea Journal of Pediatrics, Vol 48, No. 12, 2005).

Recently, sex chromosome aneuploidy is detectable by using fetal cell DNA (cell-free fetal DNA, cffDNA) and NGS, but is detected by quantifying chromosome numbers with lower accuracy than autosomal aneuploidy. Further, sequence similarity between chromosomes X and Y and sequencing bias associated with GC composition are present, and similarity between chromosome Y and other chromosomes is reduced at a signal-to-noise ratio, and the chromosome Y having a small size has many variations. Most of the cases are not easily detected, and always have a problem in classification of sex chromosome aneuploidy.

Unlike the aneuploidy on chromosomes 13, 18, and 21, it is a global trend that accuracy of judgment for XO, XXX, and XXY is not high. In fact, in the cases of Verifi (Illumina) and NIFTY (BGI), the sensitivity on chromosomes 13, 18, and 21 is 98.15% or more. However, the Verifi has 95% of the sensitivity of Monosomy X for sex chromosomes, and for XXX/XXY/XYY, the amount of data is small, and thus accuracy is not represented. In the case of NIFTY, the sensitivity of Monosomy X is represented as 75% based on the modified internal chromosome Z-score rather than based on the existing Z-score, and the remainder is not represented due to a small number of data. Even though the amount of data is small, a current algorithm does not have high accuracy, and thus it is necessary to develop an optimized new algorithm. In addition, current methods have been developed on the basis of each specific platform, and thus it is not possible to apply data of other platforms and to perform normalization using two or more data.

In addition, it is known that up to 4% of fetal DNA is able to be detected accurately which is similar to fetal autosome aneuploidy (Chiu R W et al., Maternal Plasma DNA Analysis With Massively Parallel Sequencing by Ligation for Noninvasive Prenatal Diagnosis of Trisomy 21. Clin. Chem. 2009; 56:459-63, Palomaki, G. E., et al., DNA Sequencing Of Maternal Plasma To Detect Down Syndrome: An International Clinical Validation Study. Genet Med. 2011; 13:913-20), and thus better methods and classification of data sets are needed.

Therefore, in order to solve problems of gender classification and sex chromosome aneuploidy, the present inventors found that when LOESS normalization of a GC ratio and mappability were performed, chrX and chrY values were determined using percentages of chrX and chrY, the reference line was adjusted by using internal chromosome reference to determine final Z-score regardless of the kinds of platform and data, it was possible to differentiate sex and sex chromosome abnormality with high accuracy and sensitivity, and completed the present invention.

SUMMARY OF INVENTION

An object of the present invention is to provide a method of differentiating fetal sex and fetal sex chromosome abnormality by simultaneously normalizing and analyzing all inputted data at once regardless of the type of sample and platform.

In order to achieve the foregoing objects, the present invention provides a method of differentiating fetal sex and fetal sex chromosome abnormality including: (a) performing next-generation sequencing (NGS) on two or more platforms by extracting DNA from maternal blood; (b) aligning sequences (reads) that are sequenced for each platform to a reference genome database; (c) extracting unique reads that are uniquely aligned on chromosome for each platform and calculating a percent of unique reads (UR %) relative to the total reads; (d) calculating data for each platform at the same time, setting a cut-off value, and organizing the UR(y) % values; (e) classifying male and female using the organized UR(y) %; (f) calculating partial reference chromosome (relative FGR) values using three or more autosomes that are similar in size to chromosomes X and Y; and (g) calculating Z-score using the partial reference chromosome (relative FGR) values, and calculating G score (Gscore) and M score (Mscore) based on the Z-score to differentiate sex chromosome abnormality.

BEST MODE

Unless defined otherwise, all the technical and scientific terms used herein have the same meanings as those generally understood by persons skilled in the art to which the present invention pertains. In general, nomenclature used in the present specification and experimental methods to be described below are well known and generally used in the present technical field.

In the present invention, it was confirmed that when sequencing data generated from two or more NGS platforms were normalized and aligned based on the cut-off values, and then the unique reads % aligned on the sex chromosome using partial reference chromosome was used, it was possible to differentiate fetal sex and sex chromosome abnormality with high accuracy and sensitivity.

Figure 1:
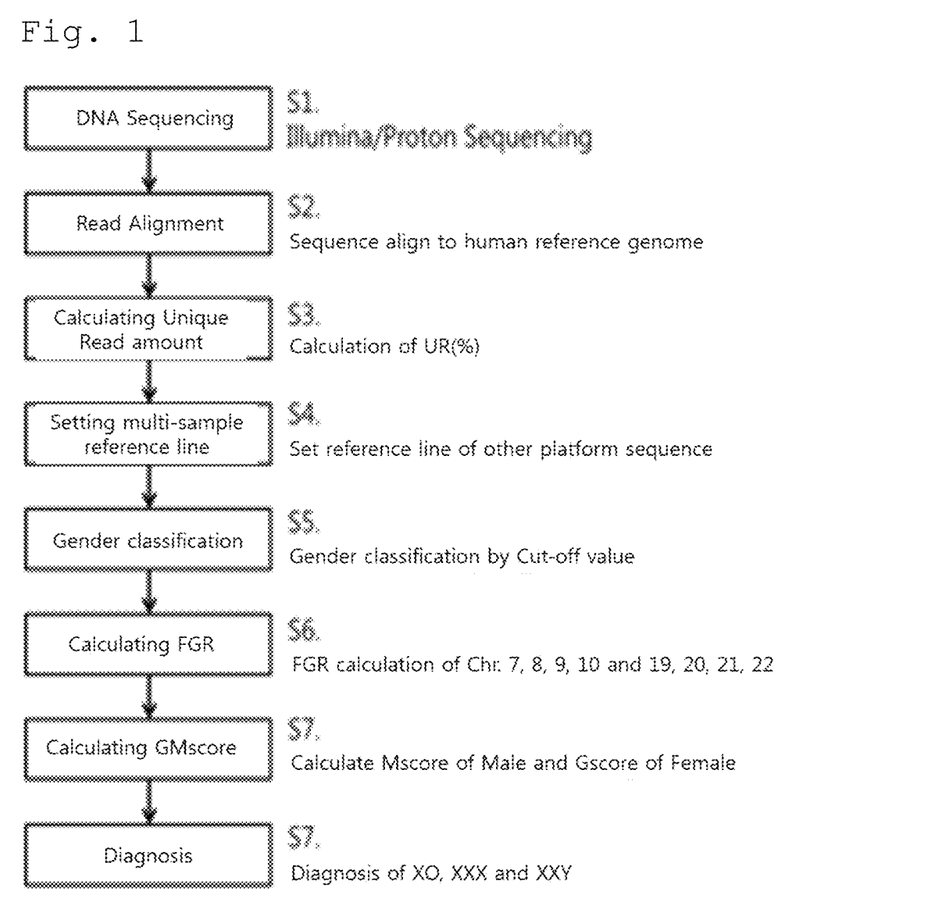
FIG. 1 is a whole flow chart for diagnosis of sex chromosome aneuploidy of the present invention.

In other words, in an exemplary embodiment of the present invention, a method of sequencing genomic DNA (gDNA) extracted from maternal blood using two or more NGS platforms, quantifying an amount of the unique reads for each chromosome to set a cut-off value based on a GC content and mappability, using chr7 to chr10 as partial reference chromosomes for quantification of chromosome X and chr19 to chr22 as partial reference chromosomes for quantification of chromosome Y, and in the case of a male, calculating Mscore (Man-score) to determine normal (XY) and Kleinfelder syndrome (XXY), and in the case of a female, calculating Gscore (Girl-score) to diagnose XXX syndrome (Triple-X, XXX) as well as Turner's syndrome (XO) and normal (XX) (FIG. 1), has been developed.

Therefore, in one aspect, the present invention relates to a method of differentiating fetal sex and fetal sex chromosome abnormality including: (a) performing next-generation sequencing (NGS) on two or more platforms by extracting DNA from a maternal biological sample; (b) aligning sequences (reads) that are sequenced for each platform to a reference genome database; (c) extracting unique reads that are uniquely aligned on chromosome for each platform and calculating a percent of unique reads (UR %) relative to the total reads; (d) calculating data for each platform at the same time, setting a cut-off value, and organizing the UR(y) % values; (e) classifying male and female using the organized UR(y) %; (f) calculating partial reference chromosome (relative FGR) values using three or more autosomes that are similar in size to chromosomes X and Y; and (g) calculating Z-score using the relative FGR values, and calculating G score (Gscore) and M score (Mscore) based on the Z-score to differentiate sex chromosome abnormality.

In the present invention, the biological sample may be selected from the group consisting of blood, plasma, serum, urine, and saliva.

In the present invention, step (a) may include: (a) separating a plasma by centrifuging the collected biological sample; (b) extracting cfDNA from the separated plasma; (c) preparing a library using the extracted cfDNA; and (d) pooling the prepared library, and then decoding the base sequence using NGS equipment.

The pooling the library of the present invention may be characterized by performing bead size selection in the case of the Illumina platform and performing E-gel size selection in the case of the Life technologies platform.

In the present invention, step (c) may include: (a) removing PCR duplication and ambiguous reads in sequencing, aligning only perfectly matched reads, and extracting a read in which a GC content and mappability are more than or equal to the cut-off value in the aligned sequence; and (b) calculating a percentage (UR(x) %) of the read that uniquely matches the chromosome X and a percentage (UR(y) %) of the read that uniquely matches the chromosome Y according to the following Equations, based on the extracted read:

$$UR(x)\% = \text{the number of chromosome } X \text{ (chrX) reads} / \text{total number of autosome reads} \times 100, \quad \text{Equation 1)}$$

$$UR(y)\% = \text{the number of chromosome } Y \text{ (chrY) reads} / \text{total number of autosome reads} \times 100. \quad \text{Equation 2)}$$

The removal of duplicated reads of the present invention may be performed by any method for removing duplication, but is preferably performed through LOESS normalization.

In the present invention, the step of analyzing the GC content and the mappability may be performed by dividing each region into 100 kb bin regions, wherein the cut-off value of the GC content may be 0.30 to 0.50, and the cut-off value of the mappability may be 20% or more.

Figure 2:
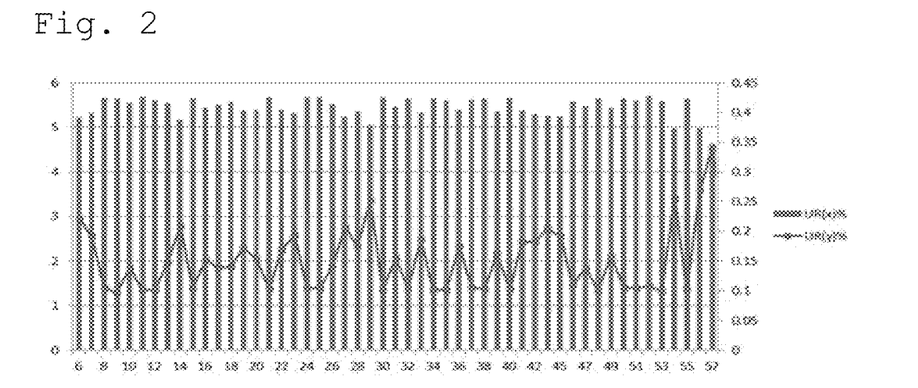
FIG. 2 shows analysis results of sex chromosome Unique Read % of samples analyzed using the HiSeq platform (Illumina). The left vertical axis represents UR(x) %, and the right vertical axis represents UR (y) %.
Figure 3:
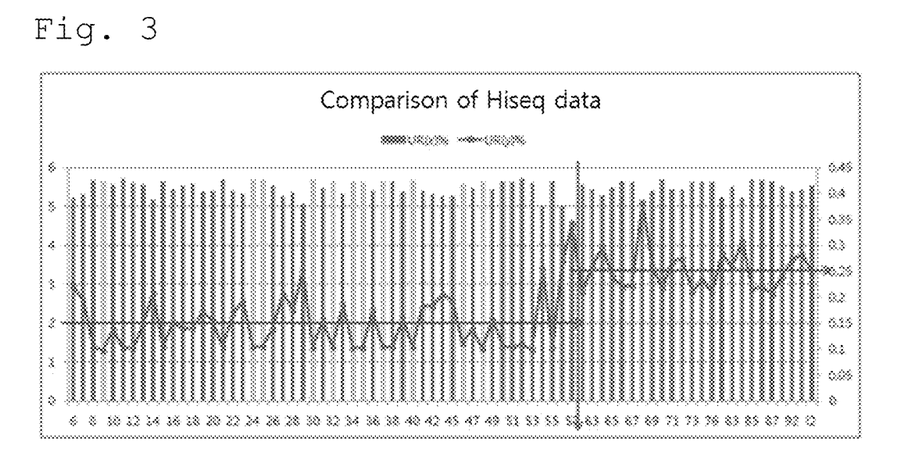
FIG. 3 shows comparison between analysis results of sex chromosome Unique Read % of two experimental sets using the HiSeq platform (Illumina).
Figure 4:
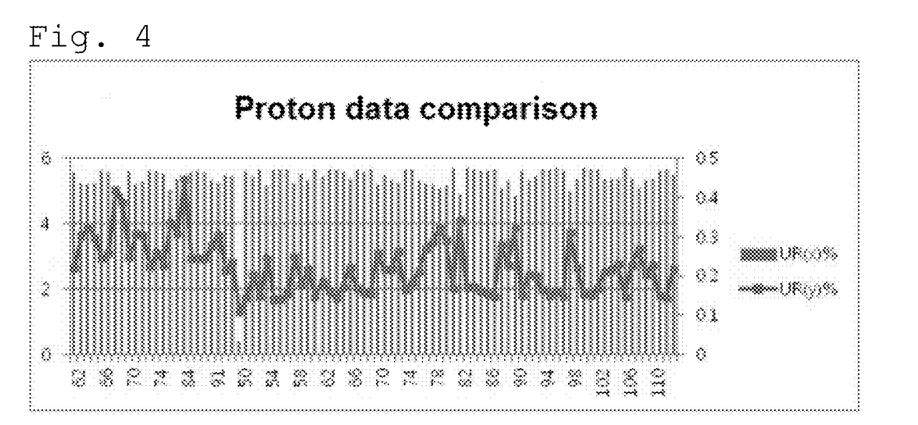
FIG. 4 shows comparison between analysis results of sex chromosome Unique Read % of two experiment sets using Ion Proton platform (Ion torrent).

In the present invention, the normalization of UR(y) % is performed on the basis of the chromosome Y in order to perform accurate classification between the chromosomes XX and XY, wherein results of a single sample (FIG. 2) may be divided into Cut-Off criteria of UR(y) %, but when the normalization is performed on a mass sample of two or more samples or another platform sample, it is not possible to set the cut-off of UR(y) % (FIGS. 3 and 4). In order to not only obtain results of various samples in one laboratory and but also take advantage of many results that are already analyzed, it is necessary to normalize the results at various platforms and at different places at once and then to classify male and female according to the Cut-Off criteria, and thus it is characterized by performing normalization by correcting UR(y) % according to the following equation, the UR(y) % being calculated for each platform:

$$UR(y)\%\_new = (UR(y)\%\_original - (\text{mean value of the three smallest } UR(y)\% \text{ values}) \quad \text{Equation 3)}$$

In the present invention, the cut-off value of (d) is preferably in the range of 0.02 to 0.06, and the most preferably 0.037.

In the present invention, the gender classification of (e) may be characterized in that when the organized UR(y) % value is more than or equal to the cut-off value, it is determined as a male, and when the organized UR(y) % value is smaller than the cut-off value, it is determined as a female.

Figure 7:
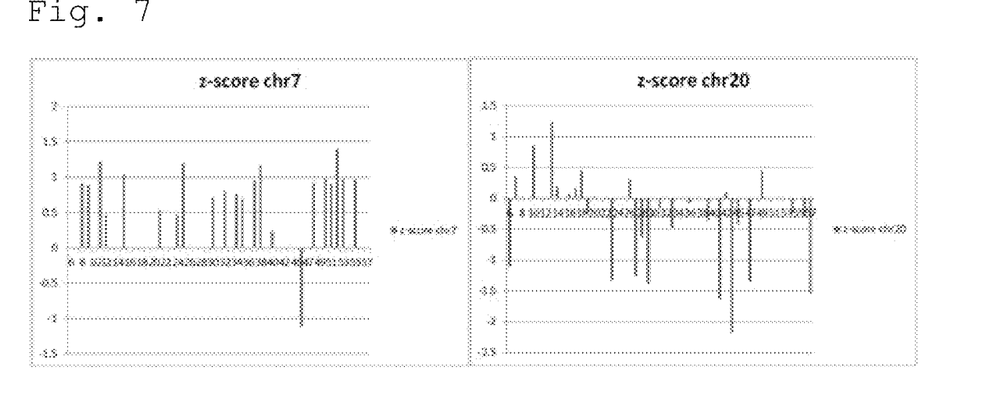
FIG. 7 is a graph showing Z-score values calculated by using only chromosome 7 (chr7) and chromosome 20 (chr20) as internal references.
Figure 8:
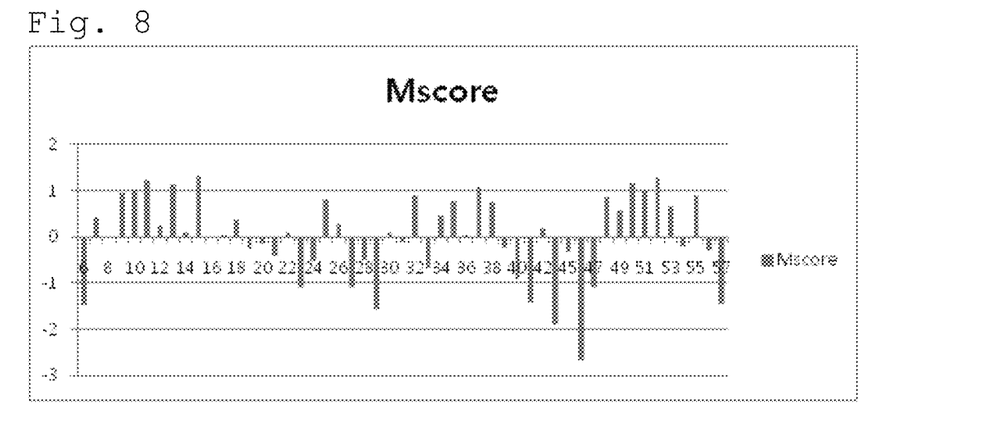
FIG. 8 is a graph showing Mscore calculated by using four internal references.
Figure 9:
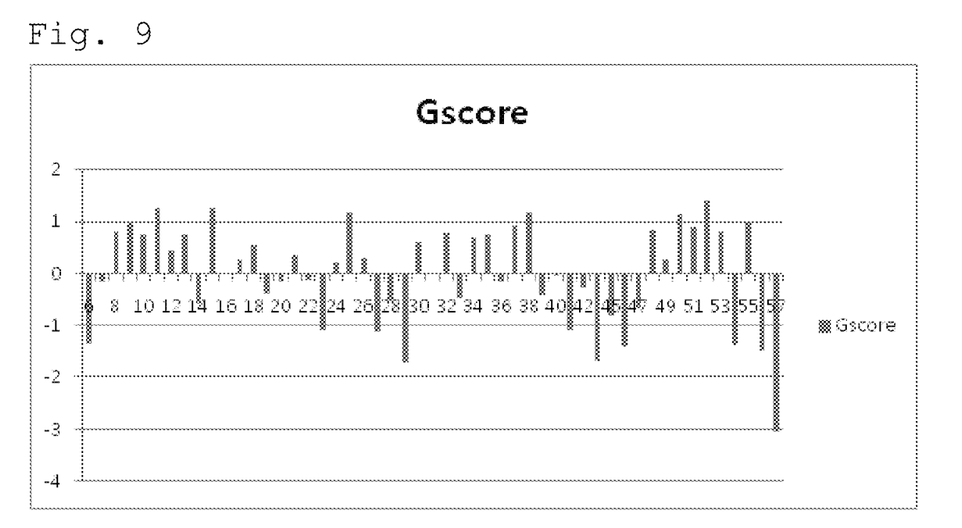
FIG. 9 is a graph showing Gscore calculated by using four internal references.

In the present invention, in order to detect sex chromosome aneuploidy, chromosomes chr19 to chr22 that are similar in size to chromosome Y are selected as internal chromosome references, chromosomes chr7 to chr10 that are similar in size to chromosome X are selected as internal chromosome references, and a partial reference chromosome (relative FGR) is calculated (Lau, T. K., et. al, J. Matern. Fetal Neonatal Med. 2012 August; 25(8):1370-4). From the paper in which Chr7 and chr20 are only selected, incorrect results are obtained since sequencing bias is so severe (FIG. 7), but it may be confirmed that a mean value of the respective values from the FGR(7) to the FGR(10) is calculated, and thus an error rate is significantly reduced (FIGS. 8 and 9).

Therefore, in the present invention, step (f) may include:
(a) selecting autosomes (chr7, chr8, chr9, and chr10) that are similar in size to sex chromosome X (chrX) as internal reference chromosomes and calculating each FGR by the following Equations:

$$FGR(7) = (UR(x)\% + UR(y)\%)/UR(7)\% \quad \text{Equation 4)}$$

$$FGR(8) = (UR(x)\% + UR(y)\%)/UR(8)\% \quad \text{Equation 5)}$$

$$FGR(9) = (UR(x)\% + UR(y)\%)/UR(9)\% \quad \text{Equation 6)}$$

$$FGR(10) = (UR(x)\% + UR(y)\%)/UR(10)\%, \quad \text{Equation 7)}$$

and
(b) selecting autosomes (chr19, chr20, chr21, and chr22) that are similar in size to sex chromosome Y (chrY) as partial reference chromosomes and calculating each FGR by the following Equations:

$$FGR(19) = (UR(x)\% + UR(y)\%)/UR(19)\% \quad \text{Equation 8)}$$

$$FGR(20) = (UR(x)\% + UR(y)\%)/UR(20)\% \quad \text{Equation 9)}$$

$$FGR(21) = (UR(x)\% + UR(y)\%)/UR(21)\% \quad \text{Equation 10)}$$

$$FGR(22) = (UR(x)\% + UR(y)\%)/UR(22)\%. \quad \text{Equation 11)}$$

In the present invention, step (g) may include: (a) differentiating sex chromosome abnormality by the following steps when the sex of the fetus is determined to be female; and a-1) calculating Z-score for each chromosome in the following Equations:

$$Zscore(7) = \{FGR(7)(\text{mean } FGR(7))\}/(stdev\ FGR(7)) \quad \text{Equation 12)}$$

$$Zscore(8) = \{FGR(8)(\text{mean } FGR(8))\}/(stdev\ FGR(8)) \quad \text{Equation 13)}$$

$$Zscore(9) = \{FGR(9)(\text{mean } FGR(9))\}/(stdev\ FGR(9)) \quad \text{Equation 14)}$$

$$Zscore(10) = \{FGR(10)(\text{mean } FGR(10))\}/(stdev\ FGR(10)) \quad \text{Equation 15)}$$

a-2) calculating Gscore using the calculated Z-score by the following Equation; and $$Gscore = \{Zscore(7) + Zscore(8) + Zscore(9) + Zscore(10)\}/4 \quad \text{Equation 16)}$$

a-3) determining that the sex chromosome is XXX when the Gscore is more than or equal to 1.5, that the sex chromosome is XX when the Gscore is more than −3 and less than 1.5, and that the sex chromosome is XO when the Gscore is less than or equal to −3;

(b) differentiating sex chromosome abnormality by the following steps when the sex of the fetus is determined to be male;

b-1) calculating Z-score for each chromosome in the following Equations:

$$Zscore(19) = \{FGR(19)(\text{mean } FGR(19))\}/(stdev\ FGR(19)) \quad \text{Equation 17)}$$

$$Zscore(20) = \{FGR(20)(\text{mean } FGR(20))\}/(stdev\ FGR(20)) \quad \text{Equation 18)}$$

$$Zscore(21) = \{FGR(21)(\text{mean } FGR(21))\}/(stdev\ FGR(21)) \quad \text{Equation 19)}$$

$$Zscore(22) = \{FGR(22)(\text{mean } FGR(22))\}/(stdev\ FGR(22)) \quad \text{Equation 20)}$$

b-2) calculating Mscore using the calculated Z-score by the following Equation; and $$Mscore=\{Zscore(19)+Zscore(20)+Z\text{-}score(21)+Zscore(22)\}/4 \quad \text{Equation 21}$$

b-3) determining that the sex chromosome is XXY when the Mscore is more than or equal to 0.7, that the sex chromosome is XY when the Mscore is more than −3 and less than 0.7.

The present invention also relates to a computer system including a computer readable medium having a plurality of instructions encrypted for controlling a computing system so as to perform a method of differentiating fetal sex and sex chromosome abnormality using two or more NGS platforms from gDNA extracted from a maternal biological sample, wherein the biological sample contains cell free nucleic acid molecules of a fetus, and the differentiating includes: aligning sequences (reads) that are sequenced for each NGS platform to a reference genome database;

extracting unique reads unique to the chromosome for each NGS platform and calculating a percent of unique reads (UR %) relative to the total reads;

calculating data for each NGS platform at the same time, setting a cut-off value, and organizing the UR(y) % values;

classifying male and female using the organized UR(y) %;

calculating partial reference chromosomes (relative FGRs) using three or more autosomes that are similar in size to chromosomes X and Y; and calculating Z-score using the relative FGR values, and calculating G score (Gscore) and M score (Mscore) based on the Z-score to differentiate sex chromosome abnormality.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples.

<Example 1> Performing Next-Generation Sequencing Using Maternal DNA

The blood collected from the mother was separated using a centrifuge to extract the plasma, and then the plasma was dissolved to prepare a library by extracting 30 ng or more of cfDNA. In the case of the Illumina platform, after combining adapters, pooling was performed using bead size selection, followed by sequencing. In the case of the Life technologies platform, pooling was performed using E-gel size selection after combining adapters, followed by sequencing.

<Example 2> Alignment of Sequences Obtained after Sequencing to Reference Genome (Human GRCh38)

Figure 10:
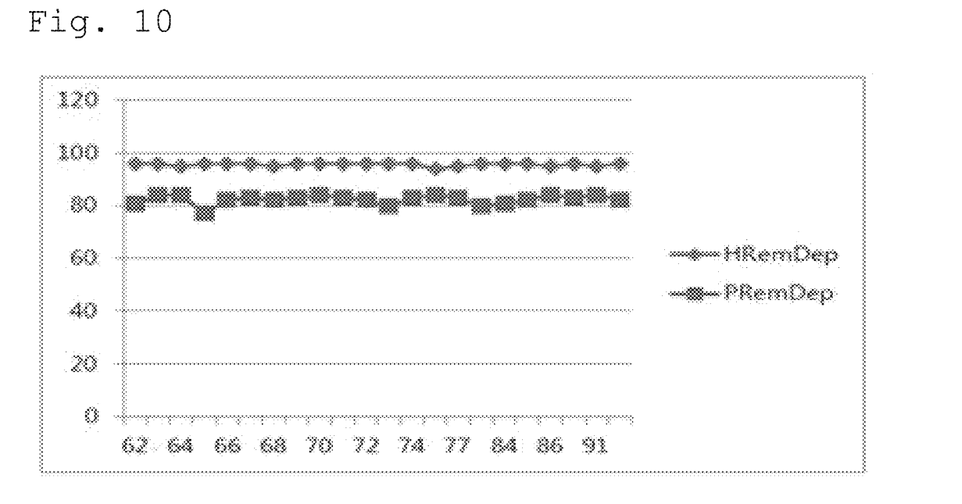
FIG. 10 is a graph showing two platforms (HiSeq of Illumina and Ion Proton of Ion torrent) from which PCR duplication is removed.
Figure 11:
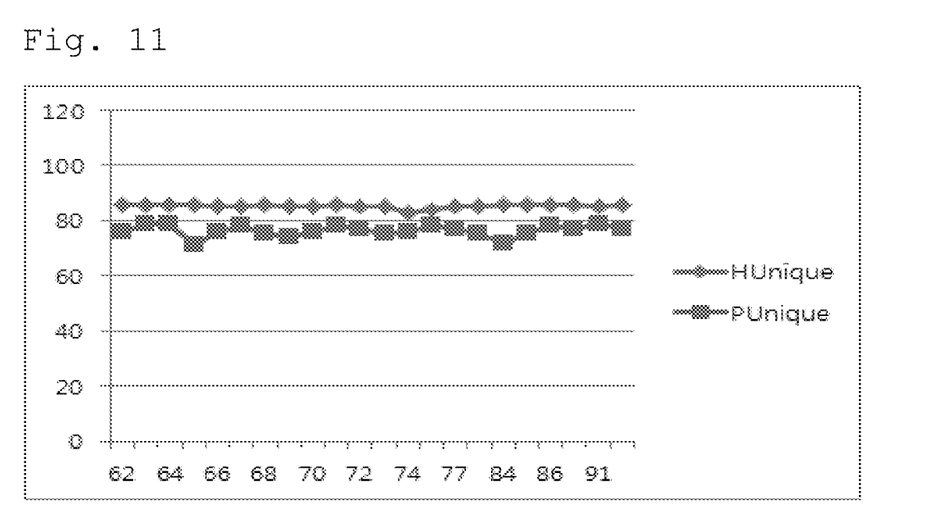
FIG. 11 is a graph showing percentages of unique reads on two platforms (HiSeq of Illumina and Ion Proton of Ion torrent).
Figure 12:
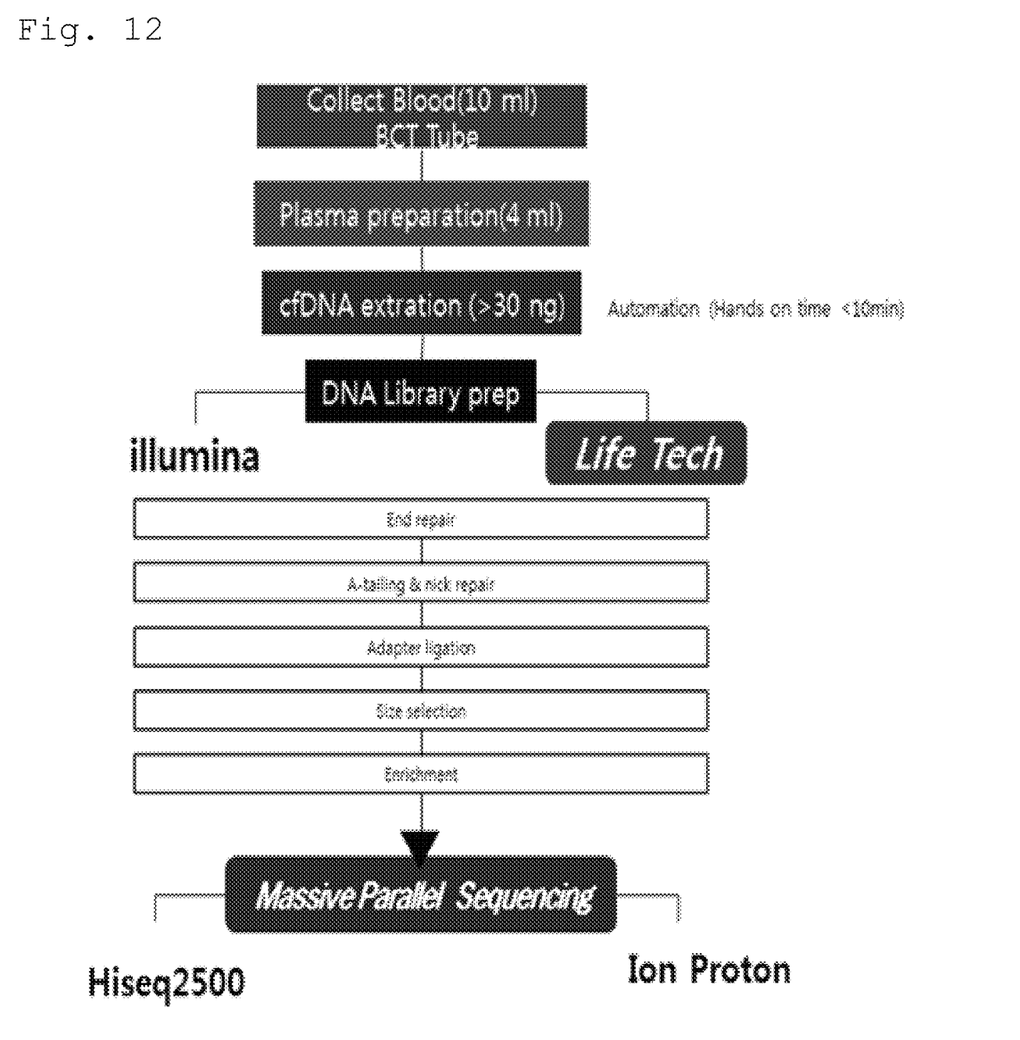
FIG. 12 is a flowchart showing a method of simultaneously performing sequencing on two platforms with one sample.

By using the latest version of GRCh38 (distributed on Dec. 24, 2013) including only about 250 gaps, alignment of the sequences was performed to remove miscellaneous sequences. The minimum unique reads were extracted using the samtools view option as well as the general picard that removes PCR duplication. In order to analyze data generated from two or more platforms, distribution of initial file size and read length was analyzed (Table 1). Since only the unique reads in all regions could not be collected by general PCR duplication removal operation (FIG. 10), after other filter options were used, about 85% of unique reads were collected for HiSeq and about 76% of unique reads were collected for Proton (Table 2).

TABLE 1

| File Size of 10M read (unit: Giga byte) | | | | | | | | | | | | | | | | | | | | | |
|---|---|---|---|---|---|---|---|---|---|---|---|---|---|---|---|---|---|---|---|---|---|
| SampleID | 77 | 91 | 64 | 73 | 92 | 72 | 76 | 62 | 68 | 67 | 83 | 74 | 86 | 85 | 71 | 66 | 87 | 63 | 65 | 70 | 69 | 84 |
| Illumina | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 |
| Proton | 2.9 | 2.9 | 2.9 | 2.9 | 2.9 | 2.9 | 2.9 | 2.9 | 2.9 | 2.9 | 2.9 | 2.9 | 2.9 | 2.8 | 2.8 | 2.8 | 2.8 | 2.8 | 2.7 | 2.7 | 2.6 | 2.6 |

TABLE 2

| | | Mappability(%) of 10M read(unit: %) | | | | | | | | | | | | | | | | | | | | | |
|---|---|---|---|---|---|---|---|---|---|---|---|---|---|---|---|---|---|---|---|---|---|---|---|
| | SampleID | 62 | 63 | 64 | 65 | 66 | 67 | 68 | 69 | 70 | 71 | 72 | 73 | 74 | 76 | 77 | 83 | 84 | 85 | 86 | 87 | 91 | 92 | Avg |
| Hiseq | HRemDep | 96 | 96 | 95 | 96 | 96 | 96 | 95 | 96 | 96 | 96 | 96 | 96 | 96 | 94 | 95 | 96 | 96 | 96 | 95 | 96 | 95 | 96 | 96 |
| | HUnique | 86 | 86 | 86 | 86 | 85 | 85 | 86 | 85 | 85 | 86 | 85 | 85 | 83 | 84 | 85 | 85 | 86 | 86 | 86 | 86 | 85 | 86 | 85 |
| Proton | PRemDep | 81 | 84 | 84 | 77 | 82 | 83 | 82 | 83 | 84 | 83 | 82 | 80 | 83 | 84 | 83 | 80 | 81 | 82 | 84 | 83 | 84 | 82 | 82 |
| | PUnique | 76 | 79 | 79 | 71 | 76 | 78 | 75 | 74 | 76 | 78 | 77 | 75 | 76 | 78 | 77 | 75 | 72 | 75 | 78 | 77 | 79 | 77 | 76 |

Figure 5:
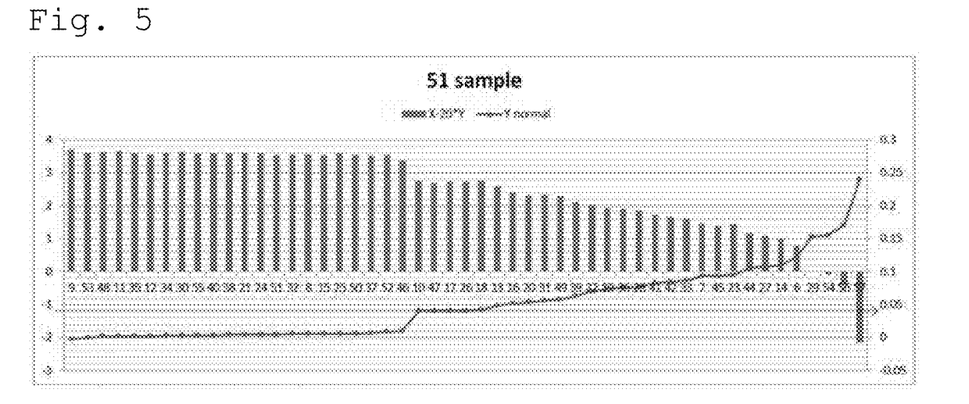
FIG. 5 is a graph showing results of gender classification on the basis of cut-off values of 51 samples using the Illumina platform.
Figure 6:
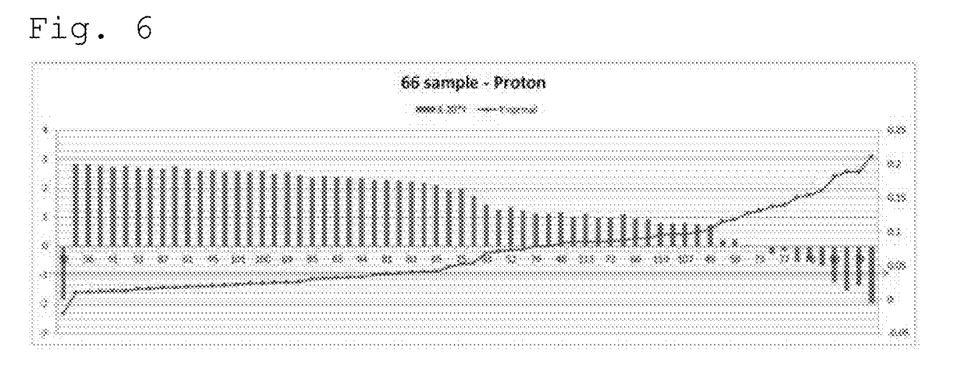
FIG. 6 is a graph showing results of gender classification on the basis of the same cut-off values as in FIG. 5 in two different experimental sets analyzed using the Ion Proton platform (Ion Torrent).

<Example 3> Data Maintenance Through Normalization of Multisamples and Multiplatform Data Each chromosome was divided into 100 kb bin regions. Then, for the GC content, regions other than 0.30<=GC content<=0.50 were removed, and for the mappability, only regions having 20% or more of mappability were selected to remove the PCR duplication and noise region. Only mean values of Z-score were used to observe the overall change. In order to establish the criteria of the bias (FIGS. 3 and 4) of experimental results obtained from difference between Illumina and Proton platforms and difference in each experiment set and location or environment, a mean value of the three smallest values of UR(y) % was obtained and the mean value was subtracted from the original value, thereby confirming that degree of variation of the value was significantly reduced by the certain cut-off value (FIGS. 5 and 6).

<Example 4> Gender Classification Using Maintained Data Values and GMscore Calculation The mean value of the same three smallest values from results performed under different experimental conditions using different platforms was set as the reference line. Then, the cut-off value of the percent of unique reads UR(y) % of chromosome Y was set in the range of 0.02 to 0.04 to classify male and female. When the sex is a female (XX), XO and XXX were differentiated by using cases that were out of normal distribution. When the sex is a male (XY), data that were out of the normal XY distribution was judged as XXY.

When regarding the UR(x) % which was the percent of unique reads of chrX, the partial reference chromosome, i.e., relative FGR, was calculated using chr7 having a similar size, and the respective Z-scores were calculated (FIG. 7), and regarding the UR(y) % which was the percent of unique reads of chrY, the partial reference chromosome, i.e., relative FGR, was also calculated using chr20 having a similar size, and the respective Z-scores were calculated (FIG. 7), the distribution degree of values was highly biased. Thus, in order to obtain the mean value of chromosomes having similar sizes, it was confirmed that the mean value of chr7, chr8, chr9, and chr10, which were similar in size to chrX, was obtained to calculate the partial reference chromosome (relative FGR) and Z-score, thereby obtaining Mscore which was the value closest to the standard value of chrX (FIG. 9). As in chrY, according to the same principle as chrX, it was confirmed that the mean value of chr19, chr20, chr21, and chr22 was obtained to calculate the relative FGR and Z-score, thereby obtaining Mscore, thereby detecting the degree of change of chrY the most accurately (FIG. 8).

<Example 5> Final Diagnosis Result by GMscore

Figure 13:
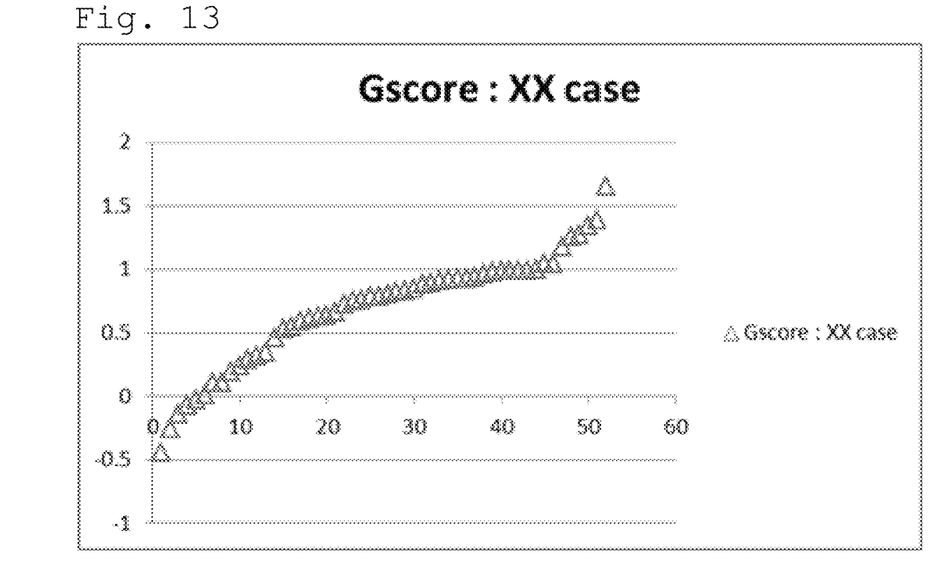
FIG. 13 is a graph showing results of sex chromosome abnormality differentiated by Gscore when classifying female in samples according to an exemplary embodiment of the present invention.
Figure 14:
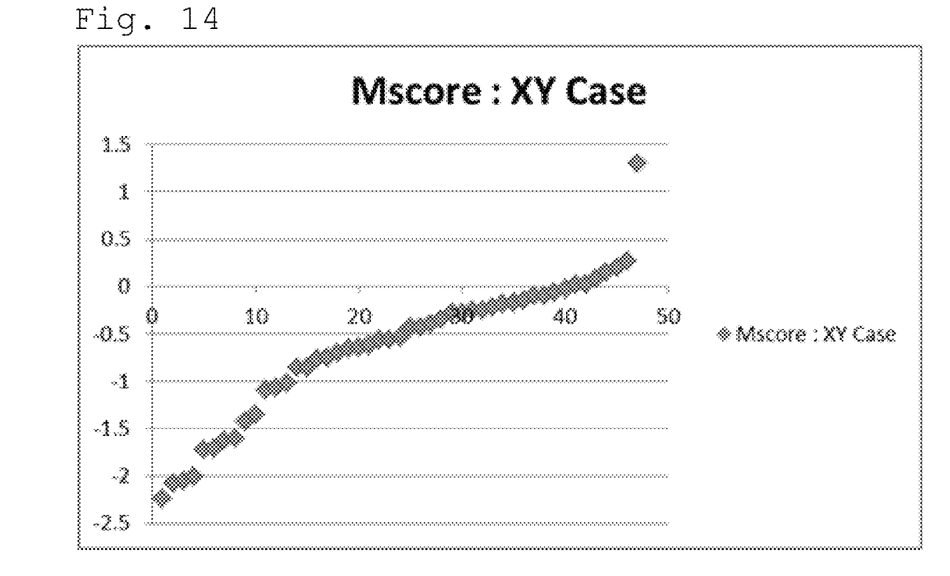
FIG. 14 is a graph showing results of sex chromosome abnormality differentiated by Mscore when classifying male in samples according to an exemplary embodiment of the present invention.

By using the methods of Examples 1 to 4, it was confirmed that 94 normal persons, 1 person with XXX genotype, and 1 person with XXY genotype (Table 3) could be clearly differentiated and all the cut-off values could be satisfied. Then, diagnosis was confirmed by amniocentesis. Even though a small sample was used, it was more difficult to obtain the sample as compared to abnormality of homologous chromosome and there was provided the score that could be clearly differentiated from the normal ratio, and thus it could be confirmed that the method was able to sufficiently judge the chromosome abnormality by only GMscore (FIGS. 13 and 14). XX could be differentiated from XXX by Gscore, and it could be predicted that XO was also able to be judged by using the cut-off value of −3 or less. Further, it was confirmed that the distribution of XXY could be sufficiently differentiated from XY by Mscore.

TABLE 3

| | Number of Samples | |
|---|---|---|
| | Female | Male |
| Normal | 49 | 45 |
| XXX | 1 | |
| XXY | | 1 |
| Total | 50 | 46 |

<Example 6> Diagnosis of Sex in Additional Sample Groups

Figure 15:
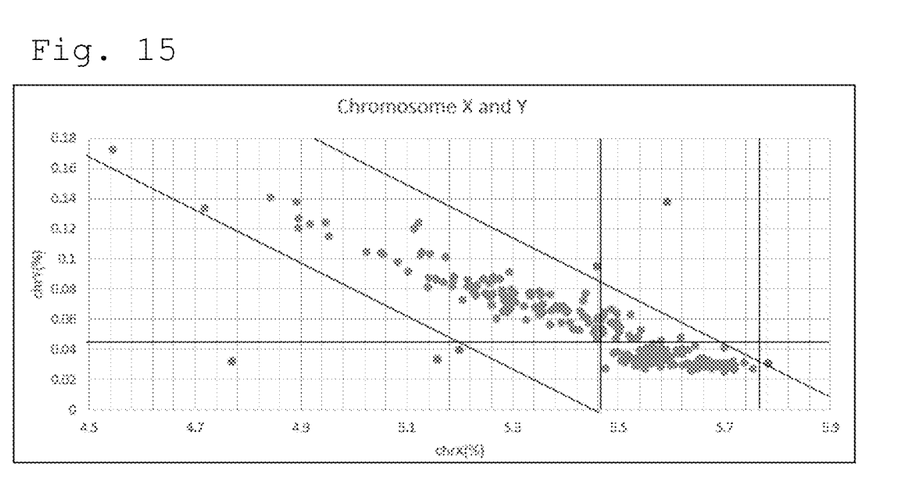
FIG. 15 is a graph showing results of differentiation of sex chromosome abnormality using chrX and chrY by adding samples according to an exemplary embodiment of the present invention.

By using the method disclosed in Example 5, it was confirmed that the sample groups (data of 3 persons with XO genotype, 1 person with XYY genotype, and 121 normal persons) shown in Table 4 were analyzed to differentiate sex and chromosome abnormality with a probability of 100% (FIG. 15).

TABLE 4

| | Female | Male |
|---|---|---|
| Normal | 101 | 114 |
| XXX | 1 | |
| XO | 3 | |
| XXY | | 1 |
| XYY | | 1 |
| Total | 105 | 116 |

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

INDUSTRIAL APPLICABILITY

The method of differentiating fetal sex and sex chromosome abnormality according to the present invention may not only increase the accuracy of gender classification using next-generation sequencing (NGS) but also increase the detection accuracy of XO, XXX, XXY, etc., which are difficult to be detected, and thus commercial use of sex chromosome together with the detection of autosome abnormality non-invasively may be increased. Therefore, the method of the present invention is useful for prenatal diagnosis capable of determining occurrence of malformation due to abnormality of fetal sex chromosomes in a fetus at an early stage.

The invention claimed is:

1. A method of detecting and diagnosing fetal sex chromosome abnormality including:
   (a) performing next-generation sequencing (NGS) from a split sample of collected maternal biological material on two or more different platforms by extracting DNA from the split sample;
   (b) aligning sequences reads that are sequenced for each platform to a reference genome database through a computer system;
   (c) extracting unique reads that are uniquely aligned on a chromosome for each platform and calculating through the computer system a percent of unique reads (UR %) relative to the total reads;
   (d) calculating data for each platform through the system at the same time from an established cut-off value to obtain a normalized UR(y) % value, wherein the calculating data comprises subtracting a mean value of three smallest percentages of unique reads that match chromosome Y from a calculated percentage of unique reads that match chromosome Y, said calculation being represented by the following equation:

$$UR(y)\%\_new = (UR(y)\%\_original - \text{mean value of the three smallest } UR(y)\% \text{ values}); \quad \text{Equation 3})$$

and whereupon the calculated percentage being a number of chromosome Y unique reads divided by one hundred times a total number of autosome reads, said calculation being represented by the following equations:

$$UR(x)\% = \text{the number of chromosome } X \text{ (chrX) reads}/ \text{total number of autosome reads} \times 100, \text{ and} \quad \text{Equation 1)}$$

$$UR(y)\% = \text{the number of chromosome } Y \text{ (chrY) reads}/ \text{total number of autosome reads} \times 100. \quad \text{Equation 2)}$$

(e) classifying male and female by comparing the normalized UR(y) % value in the data for each platform to the established cut-off value, a male gender classification is established whereupon the normalized UR(y) % value is greater than or equal to the established cut-off value and a female gender classification is established whereupon the normalized UR(y) % value is less than the established cut-off value;

(f) calculating from the gender classification partial reference chromosome (relative FGR) values for three or more predetermined autosomes, whereby a first group of three or more predetermined autosomes are used to calculate relative FGR values based upon the male gender classification and a second group of three or more predetermined autosomes different from the first group are used to calculate relative FGR values based upon the female gender classification, the FGR values being calculated relative a designated autosome of the three or more autosomes by dividing the sum of the calculated percentage of unique reads that match chromosome Y and a calculated percentage of unique reads that match chromosome X by a percentage of unique reads that match the designated autosome;

(g) calculating Z-scores and calculating at least one of a G score (Gscore) and M score (Mscore) based on the Z-score to differentiate sex chromosome abnormality from a normal sex chromosome, a calculated Z-score for a designated autosome of the three or more autosomes being calculated from a difference between the partial reference chromosome (relative FGR) value and a mean FGR value for the designated autosome, whereby the difference is divided by a standard deviation of the FGR value for the designated autosome, the Gscore and Mscore being an average of Z-scores, the Gscore being determinative of a sex chromosome abnormality when it has a value of at least one of less than or equal to −3 or greater than or equal to 1.5, the MScore being determinative of a sex chromosome abnormality when it has a value greater than or equal to 0.7.

2. The method of claim 1, wherein step (a) comprises:
(a) separating plasma by centrifuging the split sample of collected maternal biological material;
(b) extracting cfDNA from the separated plasma of the split sample of collected maternal biological material;
(c) preparing a library using the extracted cfDNA; and
(d) pooling the prepared library for each platform, and then decoding the base sequence on the two or more different platform.

3. The method of claim 1, wherein step (c) comprises: removing PCR duplication and ambiguous reads in sequence-read data, aligning only perfectly matched reads, and extracting a read in which a GC content and mappability are more than or equal to the established cut-off value in the aligned sequence.

4. The method of claim 3, wherein at least part of the aligning is performed by dividing the sequence-read data into 100 kb bin regions, wherein the cut-off value of the GC content is 0.30 to 0.50%, and the cut-off value of the mappability is 20% or more.

5. The method of claim 1, wherein the cut-off value of step (d) is 0.02~0.06%.

6. The method of claim 1, wherein step (f) comprises:
(a) selecting autosomes (chr7, chr8, chr9, and chr10) that are similar in size to sex chromosome X (chrX) as internal reference chromosomes and calculating each relative FGR by the following Equations:

$$FGR(7) = (UR(x)\% + UR(y)\%)/UR(7)\% \quad \text{Equation 4)}$$

$$FGR(8) = (UR(x)\% + UR(y)\%)/UR(8)\% \quad \text{Equation 5)}$$

$$FGR(9) = (UR(x)\% + UR(y)\%)/UR(9)\% \quad \text{Equation 6)}$$

$$FGR(10) = (UR(x)\% + UR(y)\%)/UR(10)\%, \text{ and} \quad \text{Equation 7)}$$

(b) selecting autosomes (chr19, chr20, chr21, and chr22) that are similar in size to sex chromosome Y (chrY) as partial reference chromosomes and calculating each relative FGR by the following Equations:

$$FGR(19) = (UR(x)\% + UR(y)\%)/UR(19)\% \quad \text{Equation 8)}$$

$$FGR(20) = (UR(x)\% + UR(y)\%)/UR(20)\% \quad \text{Equation 9)}$$

$$FGR(21) = (UR(x)\% + UR(y)\%)/UR(21)\% \quad \text{Equation 10)}$$

$$FGR(22) = (UR(x)\% + UR(y)\%)/UR(22)\%. \quad \text{Equation 11)}$$

7. The method of claim 1, wherein step (g) comprises:
when the female gender classification is established, fetal sex chromosome abnormalities are determined by;
a-1) calculating a Z-score for each chromosome using the following equations:

$$Zscore(7) = \{FGR(7)(\text{mean } FGR(7))\}/(\text{stdev } FGR(7)) \quad \text{Equation 12)}$$

$$Zscore(8) = \{FGR(8)(\text{mean } FGR(8))\}/(\text{stdev } FGR(8)) \quad \text{Equation 13)}$$

$$Zscore(9) = \{FGR(9)(\text{mean } FGR(9))\}/(\text{stdev } FGR(9)) \quad \text{Equation 14)}$$

$$Zscore(10) = \{FGR(10)(\text{mean } FGR(10))\}/(\text{stdev } FGR(10)) \quad \text{Equation 15)}$$

a-2) calculating Gscore using the following equation; and $$Gscore = \{Zscore(7) + Zscore(8) + Zscore(9) + Zscore(10)\}/4 \quad \text{Equation 16)}$$

a-3) determining that the sex chromosome is XXX when the Gscore is greater than or equal to 1.5, the fetal sex chromosome is XX when the Gscore is greater than −3 and less than 1.5, or the fetal sex chromosome is XO when the Gscore is less than or equal to −3;

(b) when the male gender classification is established;
b-1) calculating a Z-score for each chromosome using the following equations:

$$Zscore(19) = \{FGR(19)(\text{mean } FGR(19))\}/(\text{stdev } FGR(19)) \quad \text{Equation 17)}$$

$$Zscore(20) = \{FGR(20)(\text{mean } FGR(20))\}/(\text{stdev } FGR(20)) \quad \text{Equation 18)}$$

$$Zscore(21) = \{FGR(21)(\text{mean } FGR(21))\}/(\text{stdev } FGR(21)) \quad \text{Equation 19)}$$

$$Zscore(22) = \{FGR(22)(\text{mean } FGR(22))\}/(\text{stdev } FGR(22)) \quad \text{Equation 20)}$$

b-2) calculating the Mscore using the following equation; and $$Mscore = \{Zscore(19) + Zscore(20) + Z\text{-}score(21) + Zscore(22)\}/4 \quad \text{Equation 21)}$$

b-3) determining that the sex chromosome is XXY when the Mscore is greater than or equal to 0.7, the sex chromosome is XY when the Mscore is greater than −3 and less than 0.7.

8. The method of claim 2, wherein the split sample of collected maternal biological material is selected from the group consisting of blood, plasma, serum, urine, and saliva.

9. A computer system including a computer readable medium having a plurality of instructions for performing a method of detecting and diagnosing fetal sex chromosome abnormality, wherein the method comprises:

performing next-generation sequencing (NGS) from a split sample of collected maternal biological material on two or more different platforms by extracting DNA from the split sample;

aligning sequence reads that are sequenced for each NGS platform to a reference genome database;

extracting unique reads unique to the chromosome for each NGS platform and calculating a percent of unique reads (UR %) relative to the total reads;

calculating data for each NGS platform at the same time from an established cut-off value to obtain a normalized UR(y) % value, wherein the calculating data comprises subtracting a mean value of three smallest percentages of unique reads that match chromosome Y from a calculated percentage of unique reads that match chromosome Y, said calculation being represented by the following equation:

$$UR(y)\text{\_new} = (UR(y)\text{\_original} - \text{mean value of the three smallest } UR(y) \text{ \% values});  \quad \text{Equation 3})$$

and whereupon the calculated percentage being a number of chromosome Y unique reads divided by one hundred times a total number of autosome reads, said calculation being represented by the following equations:

$$UR(x)\% = \text{the number of chromosome } X \text{ (chr}X\text{) reads/total number of autosome reads} \times 100, \text{ and} \quad \text{Equation 1})$$

$$UR(y)\% = \text{the number of chromosome } Y \text{ (chr}Y\text{) reads/total number of autosome reads} \times 100; \quad \text{Equation 2})$$

classifying male and female by comparing the normalized UR(y) % value in the data for each platform to the established cut-off value, a male gender classification is established whereupon the normalized UR(y) % value is greater than or equal to the established cut-off value and a female gender classification is established whereupon the normalized UR(y) % value is less than the established cut-off value;

calculating from the gender classification partial reference chromosomes (relative FGRs) values for three or more predetermined autosomes, whereby a first group of three or more predetermined autosomes are used to calculate relative FGR values based upon the male gender classification and a second group of three or more predetermined autosomes different from the first group are used to calculate relative FGR values based upon the female gender classification, the FGR values being calculated relative a designated autosome of the three or more autosomes by dividing the sum of the calculated percentage of unique reads that match chromosome Y and a calculated percentage of unique reads that match chromosome X by a percentage of unique reads that match the designated autosome; and calculating Z-scores and calculating a G score (Gscore) and M score (Mscore) based on the Z-score to differentiate sex chromosome abnormality from a normal sex chromosome, a calculated Z-score for a designated autosome of the three or more autosomes being calculated from a difference between the partial reference chromosome (relative FGR) value and a mean FGR value for the designated autosome, whereby the difference is divided by a standard deviation of the FGR value for the designated autosome, the Gscore and Mscore being an average of Z-scores.

* * * * *